United States Patent [19]

Haure et al.

[11] Patent Number: 5,011,675

[45] Date of Patent: Apr. 30, 1991

[54] CONVERSION EFFICIENCY IN TRICKLE BED REACTORS

[75] Inventors: Patricia Haure; Peter L. Silveston; Robert R. Hudgins, all of Waterloo, Canada; Maxime Bellut, Nancy Cedex, France

[73] Assignee: University of Waterloo, Waterloo, Canada

[21] Appl. No.: 168,239

[22] Filed: Mar. 15, 1988

[30] Foreign Application Priority Data

Mar. 16, 1987 [GB] United Kingdom ............... 8706203

[51] Int. Cl.$^5$ ............................................. C10G 47/02
[52] U.S. Cl. ....................................... 423/659; 208/112
[58] Field of Search ......................... 423/659; 208/112

[56] References Cited

U.S. PATENT DOCUMENTS

| | | | |
|---|---|---|---|
| 3,838,524 | 10/1974 | Hencke et al. | 423/659 |
| 4,526,757 | 7/1985 | Gupta | 422/220 |
| 4,604,261 | 8/1986 | Chen et al. | 422/195 |
| 4,737,263 | 4/1988 | Chen et al. | 422/220 |

FOREIGN PATENT DOCUMENTS 218552  9/1956  Australia ............................ 423/659

Primary Examiner—Gary P. Straub
Assistant Examiner—Stuart L. Hendrickson
Attorney, Agent, or Firm—Sim & McBurney

[57] ABSTRACT

The efficiency of trickle bed reactors is improved by periodically varying the liquid flow rate through the solids bed of the reactor. The reaction rate, conversion and product concentration can be increased using the novel operating procedure.

18 Claims, 3 Drawing Sheets

CONVERSION EFFICIENCY IN TRICKLE BED REACTORS

FIELD OF INVENTION

The present invention relates to trickle bed reactors, and more particularly to improving the efficiency of such reactors.

BACKGROUND TO THE INVENTION

Trickle beds are a widely used class of three-phase chemical reactors which consist of a bed of solids, usually a catalyst, over which liquid and gas streams flow. The flow is usually downwards and concurrent, but countercurrent applications are occasionally encountered in which a gas phase is forced upwards against a descending liquid. This class of reactor finds application to many types of reaction systems. In some, one reactant is a gas and the other is a liquid under normal operating conditions. In others, the liquid phase simply serves to remove heat or the products of the reaction and all reactants enter the system in the gas phase. There are also a few cases in which the reactants enter in the liquids but one or more of the products are swept out by the gas phase.

Examples of the first type of such systems are hydrodesulphurization of refinery process streams, such as naphtha, gas oil, lube stocks, residuum, kerosene, jet fuel, etc.; hydrocracking of heavy gas oils and residuum; hydrodemetallization of gas oils and residuum; hydrogenation of edible oils and fats; tall oil hydrogenation and many other hydrogenation reactions which are part of chemical syntheses. Highly exothermic halogenation and oxidation reactions are also sometimes carried out in trickle beds.

Aqueous reactions also are carried out in this type of reactor, including oxidation of phenolic waste streams and other soluble pollutants; as are various biochemical oxidation reactions.

As noted above, a second use of trickle bed reactors is for highly exothermic reactions between gaseous reactants where the liquid phase serves as a heat sink or as a scavenger for reaction products. Examples of the former reaction are dimerization reactions, such as butylene to octanes, and the Fischer-Tropsch synthesis; while examples of the latter reaction are sulphur dioxide oxidation over activated carbon catalysts.

One common feature of all the reactions carried out in trickle gas reactors is that the gaseous reactant(s) must diffuse through the liquid to reach the catalyst surface. The liquid in the bed is either caught in pockets and is more or less stagnant or moves as a film across the particle (catalyst) surface. In the former condition, the liquid does not effectively participate in the reaction, whereas, in the latter one, the liquid provides a barrier or a resistance for the transport of the gaseous reactant(s). This barrier or resistance, in some cases, can lower the rate of reaction and thereby decrease conversion. It is not possible to eliminate the liquid phase entirely as a means of increasing conversion because its presence is essential to the system.

Conventional trickle bed design and operation recognize that there is a minimum liquid flow rate which must be maintained to completely wet the catalyst. If this minimum is not met and the reaction is exothermic, hot spots in the bed can develop through higher rates at points where the liquid barrier is no longer present. The heat so released dries out the catalyst further, increasing the rate and leading thus to the hot spot and destabilization of the trickle bed. The hot spot problem is well documented (Gianetto & Silveston, "Multiphase Reactors Theory, design and Scaleup", Hemisphere Press, 1986) and it is accepted that, for satisfactory operation, liquid flow rates must be set to be above the minimum for the reactor system.

SUMMARY OF INVENTION

Even though it is accepted practice to run trickle beds at steady state and at liquid flow rates above the minimum to keep the solid catalyst completely wetted, we have discovered, through experimentation, that the reaction rate and the conversion per unit weight or volume of catalyst, all else maintained unchanged, can be increased above that attainable at steady state. In accordance with the present invention, this result is achieved by maintaining the operating conditions in the bed continually in an unsteady state, in particular, by periodically varying the flow rate of the liquid fed to the trickle bed. Improved operation in accordance with the present invention is only obtained if the liquid rate in one part of the period or cycle permits draining of some of the liquid holdup in the bed and decreases surface wetting.

We have discovered that shutting off liquid flow during part of the cycle is possible. Indeed, we have found that switching between zero liquid flow and a flow rate which is about twice the mean flow rate gave the largest increase in the reaction rate compared to the reaction rate for steady state operation of the bed. We have further found that an abrupt reduction or shut down, or start up or flow increase is not essential, but best results are obtained when an abrupt change is used.

Periodic switching of the flow rate, surprisingly, can increase the concentration of a product of the reaction many fold in cases where the liquid serves to remove reaction products. For example, in the oxidation of $SO_2$ by air over an activated carbon catalyst, switching on the liquid flow rate for six minutes in a sixty-minute cycle (with zero liquid flow for 54 minutes), increases the concentration of the sulfuric acid produced by about 25 times.

GENERAL DESCRIPTION OF INVENTION

Figure 1:
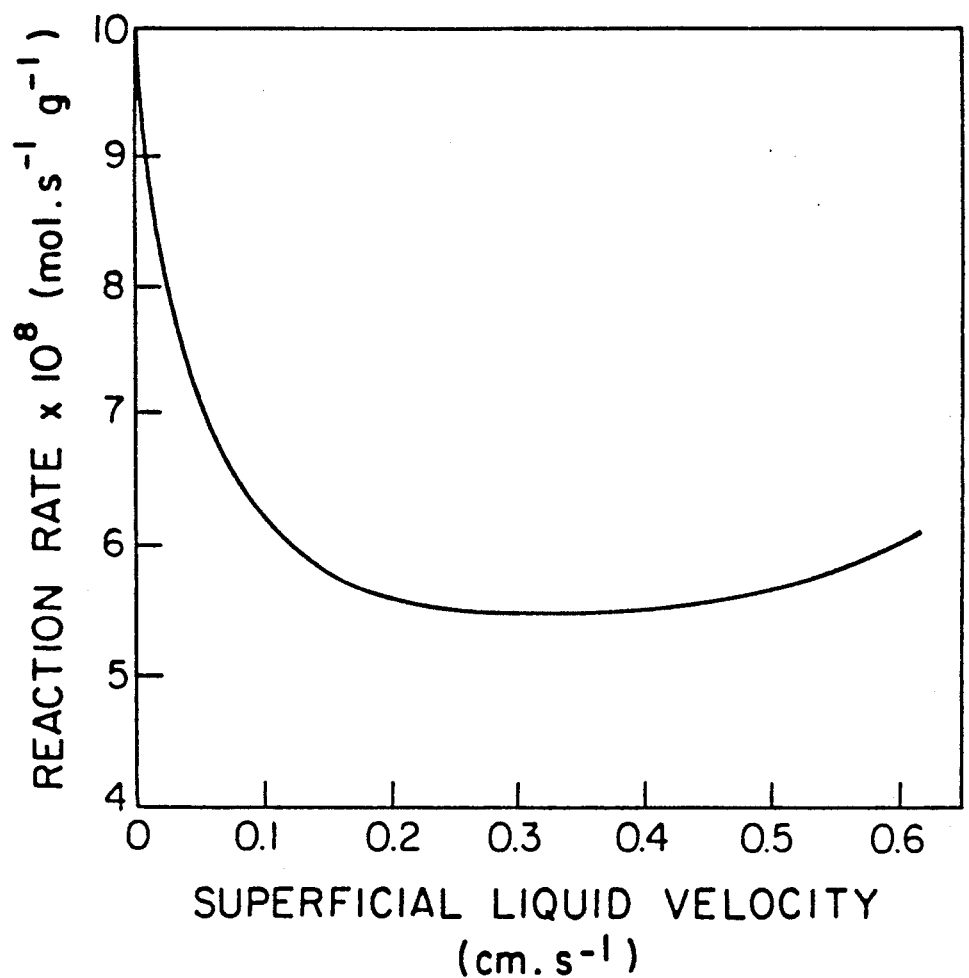
FIG. 1 is a graphical representation of the variation of reaction rate with liquid flow rate.

Improvement in reaction rate, conversion or in product concentration, in accordance with the present invention, depends critically on the period of the liquid flow cycles and the symmetry of these cycles, that is, the relative duration of those parts of the cycle when the flow is high and when it is low or zero. If the period is too short, several seconds in most cases, the improvement obtained is very small. We believe that this occurs because the bed does not have time enough to drain. On the other hand, if the cycle period is too long, there is no improvement at all and the reaction rate and conversion are well below the comparable steady state rate at the mean liquid flow rate. This happens since, if the flow is reduced or shut off for a sufficient length of time, the reaction slows down or stops. If the reaction conditions are unfavorable, the bed may overheat and dry out if the period is too long. The length of the period for these undesirable consequences depends strongly on the heat effect, reaction rate, heat capacity of the bed, amount of static liquid holdup, concentration of liquid phase reactant, etc., and may be as long as several hours.

Parts of the liquid flow cycle may be symmetrical, that is, of equal time, or asymmetrical. In the latter case, flow may be shut off or decreased for a longer time period than when flow is at a maximum. Indeed, if product concentration is important, then this is the optimum type of cycle. The explanation for this discovery is that decrease or stopping liquid flow does not shut down the reaction. There is always some static holdup in the bed, even when the liquid flow has been stopped. Since gas flow continues, the reaction proceeds. Since the lower liquid flow rate decreases catalyst wetting and decreases the transport barrier, the reaction rate (and conversion) increases until the build up of products begins to poison the catalyst. With asymmetric cycles, it is the time in the low flow part of the cycle rather than the cycle period which is important. The duration of the high flow part of the cycle must be long enough to rewet the catalyst completely and to flush out the stagnant regions of the bed. Our experiments suggest about 15 seconds are required. Consequently, highly asymmetric cycles are possible and may be desired.

This principle also operates when there is a liquid phase reactant but the limiting reactant is in the gas phase. Because liquid is retained in the bed on flow stoppage, the reaction proceeds and as already mentioned it may proceed at a higher rate until the liquid phase reactant depletion becomes important. In this situation as well as in the former one, hot spots may develop throughout the bed with exothermic reactions. However, switching to high flow in the second part of the cycle flushes products from the bed and quenches the developing hot spots. Once again, the time in the low or zero flow part of the cycle is important. However, the total cycle period must be considered as well.

Cycling of the gas flow is possible, that is, the concurrent gas flow rate can be decreased concomitantly with the liquid flow. It has been observed that gas flow changes have a relatively small influence on trickle bed performance in concurrent operation. Larger effects, however, should be found in countercurrent periodic operation. Temperature cycling is not practical because of the large thermal capacity of the trickle bed. Pressure cycling, also, offers no advantage over steady state operation.

The optimal transient operation is maintained by continually cycling the liquid flow rate through the bed between high and low values. A zero liquid flow rate as this low value is preferred.

During cycling of the liquid flow rate, periods of time at the high and low flow rates from about 10 seconds to about 2 hours may be used, preferably between about 5 minutes and about 2 hours, depending somewhat on the reaction being effected. For highly exothermic reactors, the preferred cycle period is from about 5 to about 30 minutes.

The cycles in flow rate may be of symmetric duration of low and high flow rates or asymmetric. When such asymmetric cycle duration is employed, the high flow part of the cycle preferably is shorter than the low flow part.

The changes in flow rate during the cycling operation may be abrupt or gradual, as desired. In addition, the gas flow rate also may be cycled, in phase or out of phase with the changes in liquid flow rate.

The periodic cyclic operation may be effected in a single trickle bed, in which case the liquid effluent from the bed varies with time. Alternatively, the cyclic operation may be effected in multiple parallel trickle beds, so that combined effluents from the bed can provide a constant flow with time.

A single trickle bed cyclic operation also may be carried out using a recycle of liquid effluent to obtain high concentrations of product or to decrease the use of the liquid if it is exchanged during the process.

The periodic cyclic operation may be effected in parallel trickle beds or in consecutive trickle beds so as to effect high conversion of gas phase reactant, in which the effluent from the last bed of the sequence is fed to the preceding bed and so on, to increase product concentration in the effluent.

EXAMPLES

Example 1

Measurements were made of the oxidation of sulphur dioxide by air in a trickle bed packed with fine particles of activated carbon under conditions of room (25° C.) temperature and atmospheric pressure. This reaction system was chosen as a convenient one for experimentation and is representative of the whole range of trickle bed reaction systems to which the present invention is applicable. The reaction was found to be first order in oxygen and a low order in terms of sulphur dioxide. Absorption of oxygen or its transport through the liquid phase to the carbon surface is believed to be rate controlling and is consistent with the first order kinetics for oxygen.

The activated carbon used as the catalyst was a 14 to 30 mesh material manufactured by the Calgon Corp. Before use, it was boiled in deionized water for more than an hour to eliminate fines and to saturate the particle interior with water. The water slurry then was added to a 4-cm diameter plexi-glass column with a frit plate support to build up the carbon bed a few layers at a time. Tamping and vibration were used to reach a porosity of 43%. The final bed depth was 16.4 cm and the carbon weight was 100 g.

A liquid distributor, consisting of a bundle of tiny tubes and a packing of fine glass beads, was placed in the plexi-glass column above the carbon bed to ensure perfect distribution of the liquid to the carbon bed. Observations of flow and tests with different depths of glass beads were made to verify the liquid distribution.

A liquid phase of deionized water saturated with oxygen was fed to the top of the tube distributor. An air-sulphur dioxide mixture consisting of 1.3 volume % sulphur dioxide also was fed at this point. Volumetric air flow was 1500 mL/min and was not varied throughout the experiments. The pressure above the bed was 101 kPa. The trickle bed was not insulated so that it operated at ambient temperature when no reaction occurred. Exothermicity of the oxidation raised the bed temperature by several degrees Celsius above ambient when reaction was underway, at zero liquid flow.

The extent of the oxidation was measured from the sulphur trioxide or sulphuric acid content of the liquid phase leaving the trickle bed. Phases were separated immediately below the bed. The conventional wet chemistry analytical technique was employed. A liquid sample was titrated with base for total acidity after oxidizing with hydrogen peroxide and corrected for sulphur dioxide by mixing a sample with iodine and back-titrating with sodium thiosulphate.

In order to compare periodic operation using liquid flow cycling with steady state operation, several steady state runs were performed a 98.7% volume air, 1.3% sulphur dioxide and at a gas flow rate of 1500 mL/min. At least two hours were allowed for steady state to be established and samples were taken periodically over a further several hours to test for steady state as well as to measure reproducibility. The liquid flow rate was the variable in these steady state experiments and the measurements made are shown as the rate of sulphuric acid formation per gram of catalyst in FIG. 1.

As may be seen in FIG. 1, the reaction rate passed through a minimum, just as observed by Mata and Smith (Chem. Eng. J. 22 (1981) in their experiments on this reaction system. The explanation of this minimum is that, at high liquid flow rates, turbulence increases the rate of mass transfer, so that rate increases with flow rate. On the other side of the minimum, however, wetting affects the rate. As the flow rate decreases, wetting becomes poorer, the transport resistance decreases and the reaction rate increases. The wetting phenomenon is important for this invention, not the turbulence effect.

FIG. 1 suggests that the rate of sulphuric acid formation increases up to zero flow. However, high rates at zero flow is impossible at steady state because there is no flow, but under transient operation, the formation rates are very high just after the liquid flow stops and the bed begins to drain. Given sufficient time without liquid flow, the activated carbon catalyst becomes poisoned by the adsorbed sulphur trioxide and the rate of formation goes to zero.

The trickle bed was operated periodically by switching off the liquid flow rate, but otherwise using the same gas phase composition and flow rate, and the same pressure and temperature. All measurements for this Example were made using symmetric cycles of liquid flow. The variable in the experiments was the cycle period.

Figure 2:
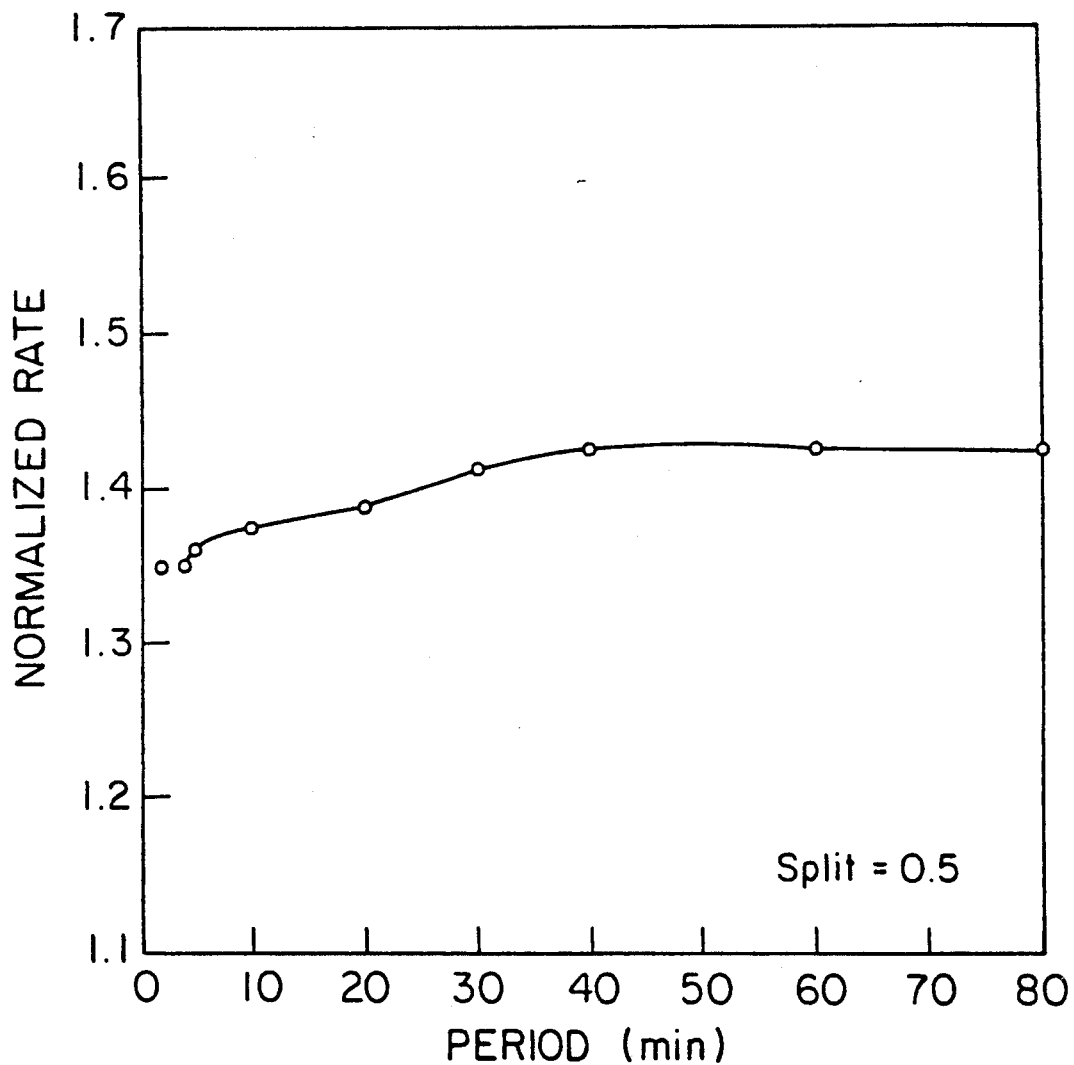
FIG. 2 is a graphical representation of the effect of liquid flow cycling on reaction rate.

The reaction system was the same as described above. The only change made was that the liquid sample was collected over one complete cycle after several cycles had been performed, so that a mixing cup or time averaged rate of sulphuric acid formation was measured. At least 10 cycles or 3 hours were allowed for the periodic operation to become reproducible. Data under liquid flow cycling were collected several times to insure reproducibility. The normalized time averaged rate was plotted against cycle period in FIG. 2. The rates shown in FIG. 2 are the time-averaged rates divided by the rates at steady state (FIG. 1) at the mean liquid flow-rates used in the cycling experiments. If periodic operation did not affect trickle bed performance, the normalized rate would be one.

FIG. 2 shows that switching the liquid flow rate on and off substantially increases the reaction rate. At a period of 40min, the increase is 30%. There is very little change in the rate improvement over the range of periods studied. Even at a period of sixty minutes, which means there is zero liquid flow through the bed for 30 minutes, FIG. 2 shows the time average rate is 25% greater than the rate at steady state.

Example 2

A further set of experiments was conducted with measurements were carried out as described in Example 1. Equipment, catalyst feed steams were also the same. The only difference was in time during which liquid, e.g. water, flowed through the trickle bed of the activated carbon catalyst. The flow rate during this portion of the cycle was kept constant at 226 mL/min. Two variables were investigated, namely the cycle period and the cycle split. The period varied from 2 to 110 minutes, while the cycle split varied from 0.1 to 0.5 (i.e. the fraction of cycle period in which liquid flows through the bed while in the remainder of the cycle, only gas containing air +1.3 vol.% $SO_2$ passes through the bed). The latter is the split corresponding to symmetrical cycling which was the operation described in Example 1.

Figure 3:
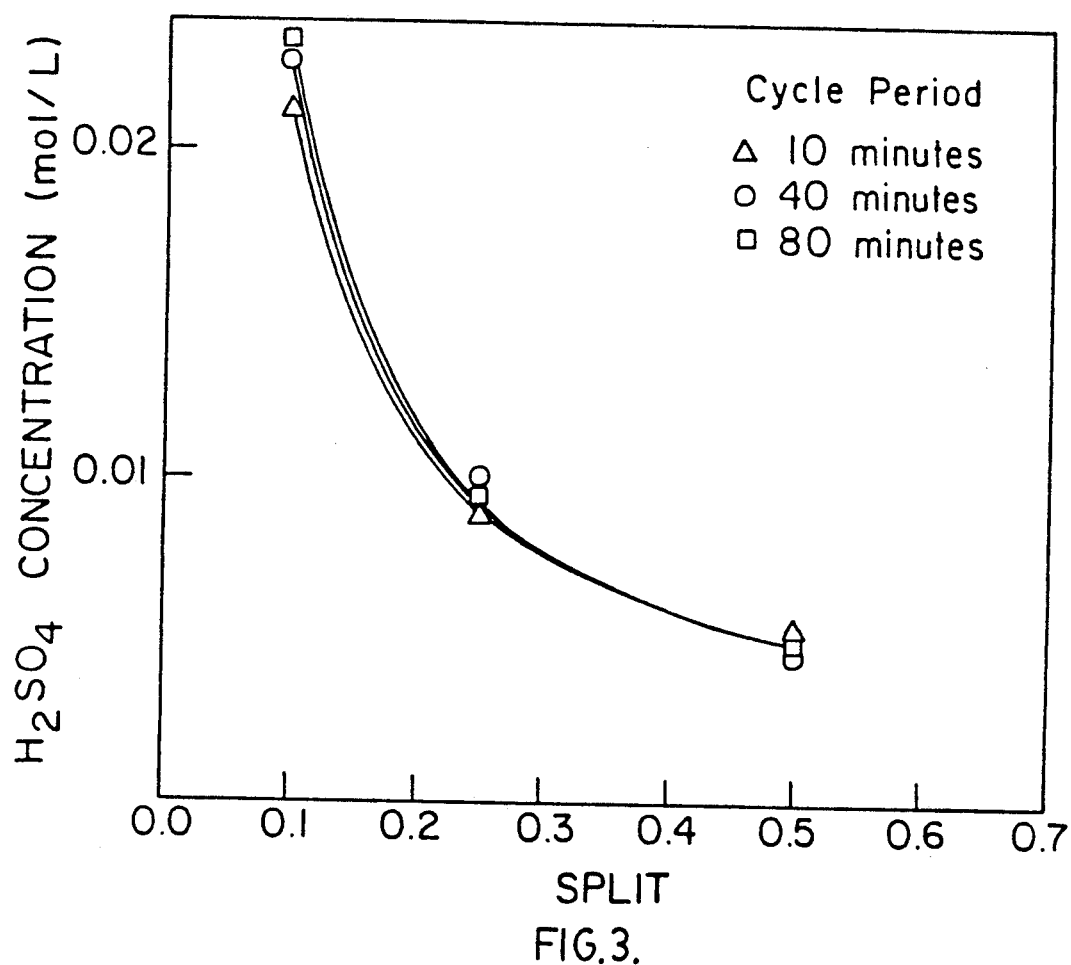
FIG. 3 is a graphical representation of the influence of two variables on product concentration.

The $H_2SO_4$ concentration in mixed liquid leaving the trickle bed reactor was plotted versus cycle split, as shown in FIG. 3. The influence of the two variables on the mixing cup $H_2SO_4$ concentration leaving the trickle bed can be seen from this Figure. It is to be noted the first liquid leaving the bed once liquid flow resumes is at least twice the mixing cup value. It can be seen from FIG. 3 that cycle period has only a small effect on concentration while cycle split is the important variable. Using an asymmetric cycle with a split less than 0.5, increases the acid concentration. Indeed a split of 0.1 increases the concentration by at least 5 times. Even smaller splits can be used to raise the concentration further. There is a minimum split which depends on the period used if water is the flushing fluid. This limit is set by poisoning of the activated carbon catalyst. Our experiments suggest this limit is a split of 0.01 which results in a 0.4N acid solution.

The acid concentrations shown in FIG. 3 are low. The challenge is to produce acid concentrations that are greater than 1N. This can be accomplished readily by recycling the acid or by using multiple beds in parallel and employing the effluent from the first bed as the feed to the second and so on. The limit on concentration is achieved only by poisoning of the catalyst.

This example offers a means of generating concentrated sulfuric acid from $SO_2$ containing stack gases without the use of special adsorbents that must be chemically regenerated outside of the trickle bed.

An advantage of this invention over a conventional adsorption process operating at steady state is that the solubility of oxygen decreases as the acid strength increases. Thus, using acid in place of water reduces the rate of $SO_2$ oxidation because oxygen is supplied to the catalyst surface from the liquid phase. In our invention, this limitation will be much less important because the catalyst surface with no liquid flow is not wetted so there is direct contact between air and the catalyst.

The present invention is not limited to $SO_2$ oxidation over activated carbon as the following Example 3 demonstrates. Indeed, as pointed out above, the present invention can be used on any trickle bed process and will provide substantial benefits as long as conditions mentioned apply.

Example 3

The Fischer-Tropsch synthesis converts a mixture of hydrogen and carbon monoxide into a range of hydrocarbon and occasionally alcohols ranging from methane (and methanol) up to high molecular weight waxes.

This reaction is often conducted in the liquid phase because of the high heat of reaction which can be more easily handled in a liquid system than in a gas one. A further reason is that the high molecular weight material tends to collect on the catalyst and poison its activity. Recent studies carry out this reaction in a slurry in which the liquid phase is an oil, e.g. naphtha, which dissolves the waxes. Slurry reactors also provide better control because of their thermal inertia and rapid heat transfer. However, the presence of the liquid decreases the rate of transfer of the reactant gases to the catalyst and this controls ultimately the reaction rate.

We have conducted the Fischer-Tropsch synthesis in a trickle bed reactor of the dimensions given in Example 1. However, the reactor was fabricated out of stainless steel so pressures up to 1 MPa could be used. Details of the trickle bed were similar to the one previously described in Example 1. The trickle bed contained 12 gm of catalyst of composition $Fe:Ca:K_2O$ in the ratio of 100:20:1. The remainder of the bed was filled with about 98 gm of glass beads, also 20/40 mesh. A jacket heater surrounding the steel reactor maintained the temperature at about 246° C. Superficial velocity through the bed was 2 cm/s while the liquid flow rate was 0.3 cm/s. A commercial diesel oil (41.3 API gravity) was used as the liquid. After passing through the catalyst bed, the reaction products, unreacted gas and circulating oil were passed to a gas separator.

Measurements were made only of the lighter hydrocarbons produced and it was assumed that their solubility in the oil was negligible. A Carle gas chromatograph was employed.

Two experiments were performed. In the first experiment, the trickle bed operated at steady state under the conditions just given. The feed gas contained 65% $H_2$ with the remainder CO. Conversion was about 15% based on carbon monoxide. Rates of reaction were 0.2, 0.12, 0.1 and 0.06 mmol $h^{-1}g$ cat.$^{-1}$ for methane ($C_1$), $C_2$, $C_3$ and $C_4$. Higher hydrocarbons were not measured because of their possible solubility in the oil phase.

In the second experiment, symmetrical cycling was employed with a period of 10 minutes. It was observed that temperature rose by 10° to 20° C. in the bed during the time the oil flow was interrupted. This limited the period that could be used. Reaction rates determined from the gas phase measurements showed a large increase. The methane formation rate went from 0.2 to 0.3 mmol $h^{-1}g$ cat.$^{-1}$, $C_2$ increased to about 0.17 while $C_3$ went to 0.12 and $C_4$ reached 0.08 mmol $h^{-1}g$ cat.$^{-1}$. Thus, the increase in rate attributable to periodic interruption of flow ranged from 20 to 30%.

This example shows the same order of improvement that was exhibited with the $SO_2$ oxidation system that was much more intensively studied.

SUMMARY OF DISCLOSURE

In summary of this disclosure, the present invention provides a novel method of operating trickle bed reactors which produces improved results. Modifications are possible within the scope of this invention.

What we claim:

1. A method of effecting a chemical reaction in a trickle bed reactor by flowing liquid and gaseous streams over a bed of solids which comprises:
   first flowing said liquid stream downwardly over said bed of solids at a flow rate which is less than that necessary to maintain said bed of solids completely wetted to cause the formation of stagnant liquid pockets in said bed and exposure of dry solids to said flowing gas stream for a period of time which permits said chemical reaction to continue,
   then flowing said liquid stream downwadly over said bed of solids at a higher flow rate than that necessary to maintain said bed of solids completely wetted and for a period of time sufficient to rewet the solids completely, quench any hot spots which have developed in said bed and to flush out stagnant regions of the bed, and
   subsequently repeating said steps of lesser flow rate flow of said liquid stream over said bed of particles and higher flow rate of said liquid stream over said bed of particles, whereby said chemical reaction is effected more efficiently than flowing said liquid stream over said bed of particles at a constant flow rate which is at least that necessary to maintain said bed of particles completely wetted.

2. The process of claim 1 wherein the low value of the rate of flow of liquid is a zero flow rate of liquid feed to said bed.

3. The process of claim 1 wherein the period of said high and low values of flow rate is from about 10 seconds to about 2 hours.

4. The process of claim 3 wherein said period is from about 5 minutes to about 2 hours.

5. The process of claim 3 wherein said chemical reaction is an exothermic one and said period is from about 5 minutes to about 30 minutes.

6. The process of claim 1 wherein the period of high flow rate and of low flow rate portions of the cycle are of symmetric duration.

7. The process of claim 1 wherein the period of high flow rate and of low flow rate portions of the cycle are of asymmetric duration.

8. The process of claim 7 wherein the high flow rate portion of the cycle is shorter than the low flow rate portion.

9. The process of claim 1 wherein abrupt changes in flow rate occur.

10. The process of claim 1 wherein gradual changes in flow rate occur.

11. The process of claim 1 wherein the flow rate of both liquid and gas through the bed is cycled between high and low values.

12. The process of claim 11 wherein the changes in gas and liquid flow rates are in phase.

13. The process of claim 11 wherein the changes in gas and liquid flow rates are out of phase.

14. The process of claim 1 wherein the flow rate of liquid through the bed is cycled between high and low values and the flow rate of gas through the bed is maintained substantially constant.

15. The process of claim 1 which is carried out in a single trickle bed to result in a flow rate of liquid effluent from the bed which varies with time.

16. The process of claim 1 which is carried out in multiple parallel trickle beds to result in a flow rate of combined liquid effluent from the parallel beds which is substantially constant with time.

17. The process of claim 1 which is carried out in a single trickle bed and wherein liquid effluent is recycled.

18. The process of claim 1 which is carried out in multiple consecutive trickle beds wherein the effluent from one is fed to the next bed.

* * * * *